(12) United States Patent
Matsumura et al.

(10) Patent No.: US 9,921,227 B2
(45) Date of Patent: *Mar. 20, 2018

(54) BIOLOGICAL INFORMATION MEASUREMENT METHOD

(71) Applicant: Panasonic Healthcare Holdings Co., Ltd., Minato-ku, Tokyo (JP)

(72) Inventors: Keisuke Matsumura, Ehime (JP); Masumi Aono, Ehime (JP); Kaoru Shigematsu, Ehime (JP); Yoshiki Takeuchi, Ehime (JP); Takahiro Watanabe, Ehime (JP)

(73) Assignee: Panasonic Healthcare Holdings Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/409,486

(22) Filed: Jan. 18, 2017

(65) Prior Publication Data

US 2017/0122956 A1 May 4, 2017

Related U.S. Application Data

(63) Continuation of application No. 13/978,031, filed as application No. PCT/JP2012/001224 on Feb. 23, 2012, now Pat. No. 9,587,989.

(30) Foreign Application Priority Data

Mar. 1, 2011 (JP) .................................. 2011-043480
Mar. 1, 2011 (JP) .................................. 2011-043482
Mar. 1, 2011 (JP) .................................. 2011-043483

(51) Int. Cl.
*G01K 1/00* (2006.01)
*G01N 33/66* (2006.01)
(Continued)

(52) U.S. Cl.
CPC .......... *G01N 33/66* (2013.01); *F24F 11/0012* (2013.01); *G01K 1/14* (2013.01); *G01N 27/3274* (2013.01); *G01N 33/48792* (2013.01)

(58) Field of Classification Search
USPC ....... 374/1, 208, 141, 163, 142; 435/286.11, 435/287.1
See application file for complete search history.

(56) References Cited

U.S. PATENT DOCUMENTS 7,354,429 B2    4/2008  Sparks et al.
8,105,841 B2    1/2012  Blais et al.
(Continued)

FOREIGN PATENT DOCUMENTS

JP    2002-521692 A    7/2002
JP    2006-511788 A    4/2006
(Continued)

OTHER PUBLICATIONS

The International Search Report of Int'l Appln. No. PCT/JP2012/001224 dated Apr. 17, 2012.
(Continued)

*Primary Examiner* — Mirellys Jagan
(74) *Attorney, Agent, or Firm* — Shinjyu Global IP

(57) ABSTRACT

Biological sample measurement device includes biological sample measuring instrument, and temperature information supply instrument which supplies temperature information regarding a measurement environment to biological sample measuring instrument and has holding portion of biological sample measuring instrument on the upper surface thereof. Biological sample measuring instrument has main body case, measurement unit provided inside main body case, a control unit connected to the measurement unit, and temperature information reception unit connected to the control unit. Holder has temperature sensor, and temperature infor-
(Continued)

mation transmission unit which is connected to temperature sensor and transmits the temperature information to temperature information reception unit.

6 Claims, 19 Drawing Sheets

(51) Int. Cl.
*G01N 27/327* (2006.01)
*G01N 33/487* (2006.01)
*G01K 1/14* (2006.01)
*F24F 11/00* (2018.01)

(56) References Cited

U.S. PATENT DOCUMENTS

| | | |
|---|---|---|
| 8,696,597 B2 | 4/2014 | Neel et al. |
| 8,915,850 B2 | 12/2014 | Heller et al. |
| 2002/0060247 A1 | 5/2002 | Krishnaswamy et al. |
| 2006/0229502 A1 | 10/2006 | Pollock et al. |
| 2007/0025877 A1 | 2/2007 | Hansen |
| 2007/0172388 A1 | 7/2007 | Padmanabhan et al. |
| 2007/0233395 A1 | 10/2007 | Neel et al. |
| 2010/0036213 A1 | 2/2010 | Rieth |
| 2010/0268475 A1 | 10/2010 | Kusumoto |
| 2010/0283488 A1 | 11/2010 | Nakamura et al. |
| 2010/0307916 A1 | 12/2010 | Ramey et al. |
| 2011/0210951 A1 | 9/2011 | Guthrie et al. |
| 2013/0105334 A1 | 5/2013 | Nakamura et al. |

FOREIGN PATENT DOCUMENTS

| | | |
|---|---|---|
| JP | 2007-526440 A | 9/2007 |
| JP | 2009-532706 A | 9/2009 |
| WO | 00/007013 A2 | 2/2000 |
| WO | 03/091717 A1 | 11/2003 |
| WO | 2005/000114 A2 | 1/2005 |
| WO | 2009/119116 A1 | 10/2009 |
| WO | 2009/119118 A1 | 10/2009 |
| WO | 2010/049669 A1 | 5/2010 |

OTHER PUBLICATIONS

The Japanese Office Action for 2013-502183 dated Feb. 24, 2015.
Notice of Allowance from the corresponding Japanese Patent Application No. 2013-502183 dated Sep. 29, 2015.

BIOLOGICAL INFORMATION MEASUREMENT METHOD

CROSS-REFERENCE TO RELATED APPLICATIONS

This application is a continuation application of and claims priority to U.S. application Ser. No. 13/978,031 filed on Jul. 2, 2013, which is a National Stage Application under 35 U.S.C. § 365 of International Application PCT/JP2012/001224, with an international filing date of Feb. 23, 2012, which claims priority to Japanese Patent Application No. 2011-043480 filed on Mar. 1, 2011, Japanese Patent Application No. 2011-043482 filed on Mar. 1, 2011, and Japanese Patent Application No. 2011-043483 filed on Mar. 1, 2011. The entire disclosures of U.S. application Ser. No. 13/978,031, International Application PCT/JP2012/001224, Japanese Patent Application No. 2011-043480, Japanese Patent Application No. 2011-043482, and Japanese Patent Application No. 2011-043483 are hereby incorporated herein by reference.

TECHNICAL FIELD

The present invention relates to a biological sample measurement device which includes a biological sample measuring instrument and a temperature information supply instrument supplying temperature information to the biological sample measuring instrument.

BACKGROUND ART

A biological sample measuring instrument of the related art will be described. The biological sample measuring instrument of the related art has a mounting portion of a biological sample measurement sensor performing a measurement of a biological sample, a measurement unit connected to the mounting portion, a control unit connected to the measurement unit, and a temperature sensor connected to the control unit (for example, see PTL 1). The control unit of the biological sample measuring instrument performs controls so as to correct a measured value measured by the measurement unit on the basis of a temperature detected by the temperature sensor.

This is because a reaction in the biological sample measurement sensor largely fluctuates depending on the temperature.

However, in the biological sample measuring instrument of the related art, the temperature sensor is arranged inside the biological sample measuring instrument. For this reason, an increase in temperature of a component (for example, a component, such as the control unit) mounted inside the biological sample measuring instrument may affect the temperature to be detected by the temperature sensor. As a result, the measured value may be corrected by a temperature different from the environment temperature of a reaction portion of the biological sample measurement sensor outside the biological sample measuring instrument, and in this case, the measured value may vary.

CITATION LIST

Patent Literature

PTL 1: Pamphlet of International Publication No. WO2005/000114

SUMMARY OF THE INVENTION

The invention has been accomplished in consideration of the above-described problem, and an object of the invention is to suppress variation in the measured value.

A biological sample measurement device of the invention includes a biological sample measuring instrument, and a temperature information supply instrument which supplies temperature information regarding a measurement environment to the biological sample measuring instrument and has a holding portion of the biological sample measuring instrument on the upper surface thereof. The biological sample measuring instrument has a main body case, a measurement unit provided inside the main body case, a control unit connected to the measurement unit, and a temperature information reception unit connected to the control unit. The temperature information supply instrument has a temperature sensor, and a temperature information transmission unit which is connected to the temperature sensor and transmits the temperature information to the temperature information reception unit.

The biological sample measuring instrument of the invention includes the main body case, the measurement unit provided inside the main body case, the control unit connected to the measurement unit, and the temperature information reception unit which is connected to the control unit and receives the temperature information regarding the measurement environment from the temperature information supply instrument.

The temperature information supply instrument of the invention includes the first temperature sensor, and the temperature information transmission unit which is connected to the first temperature sensor and transmits the temperature information regarding the measurement environment to the temperature information reception unit.

DESCRIPTION OF EMBODIMENTS

Figure 1:
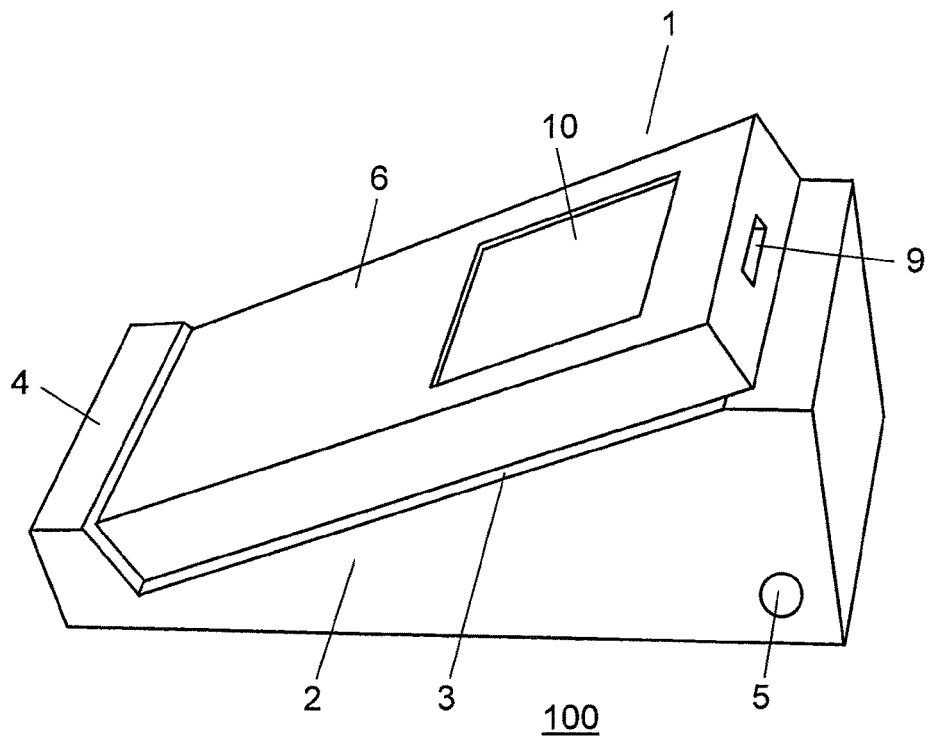
FIG. 1 is a perspective view showing the configuration of a biological sample measurement device according to a first embodiment of the invention.

Hereinafter, embodiments of the invention will be described referring to the drawings. It should be noted that the invention is not limited to these embodiments.

First Embodiment

Figure 2:
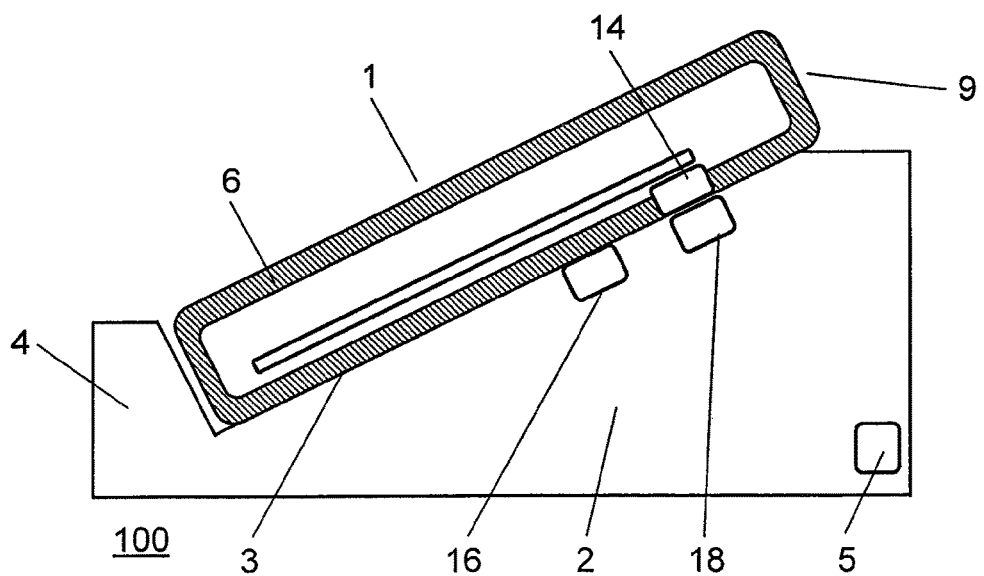
FIG. 2 is a diagram showing the sectional configuration of the biological sample measurement device according to the first embodiment of the invention.
Figure 3:
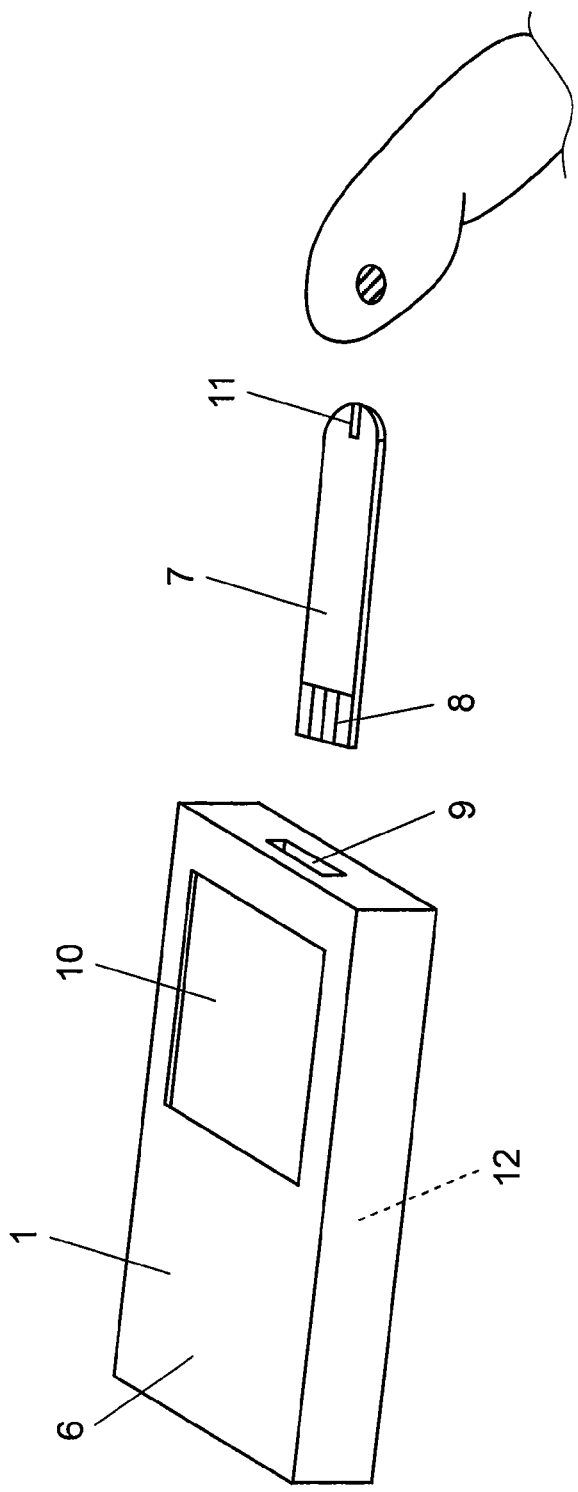
FIG. 3 is a perspective view showing the configuration of a biological sample measuring instrument according to the first embodiment of the invention.

FIG. 1 is a perspective view showing the configuration of biological sample measurement device 100 according to a first embodiment of the invention. FIG. 2 is a diagram showing the sectional configuration of biological sample measurement device 100. FIG. 3 is a perspective view showing the configuration of biological sample measuring instrument 1 according to the first embodiment of the invention.

As shown in FIG. 1, biological sample measurement device 100 includes biological sample measuring instrument (hereinafter, simply referred to as a measuring instrument) 1 which measures, for example, blood glucose level from blood, and holder 2 which doubles as a temperature information supply instrument supplying temperature information to measuring instrument 1.

Measuring instrument 1 is held in holding portion 3 provided on the upper surface of holder 2, for example, when moving between patient's rooms at a hospital.

As shown in FIGS. 1 and 2, holding portion 3 has a surface which is inclined downward from the leading end to the rear and (from the right side to the left side when viewed toward the Figures) In a lower end portion of the inclination, stopper 4 which receives measuring instrument 1 in contact with the inclined surface of holding portion 3 is provided.

Holder 2 has temperature sensor 5 in an outer circumferential portion near the bottom portion thereof. That is, in this embodiment, temperature sensor 5 (first temperature sensor) is provided outside measuring instrument 1.

As shown in FIG. 3, measuring instrument 1 has plate-shaped main body case 6. In a leading end portion of main body case 6, sensor mounting portion 9 into which connection terminal 8 of thin plate-shaped blood glucose level sensor 7 (an example of a biological sample measurement sensor) is inserted is provided. On the upper surface of main body case 6, display unit 10 which displays the blood glucose level is provided.

A measurer mounts connection terminal 8 of blood glucose level sensor 7 in sensor mounting portion 9, and spots blood in spotting portion 11 at the leading end of blood glucose level sensor 7 in this state. Accordingly, the blood glucose level at this time is measured by measurement unit 12 embedded in main body case 6.

Figure 4:
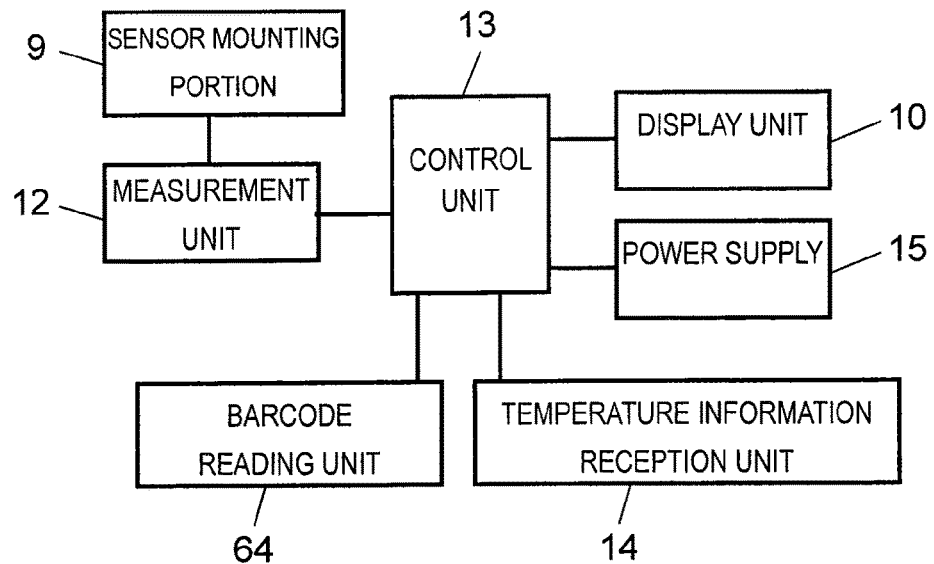
FIG. 4 is a functional block diagram of the biological sample measuring instrument according to the first embodiment of the invention.

FIG. 4 is a functional block diagram of biological sample measuring instrument 1 according to the first embodiment of the invention.

As shown in FIG. 4, sensor mounting portion 9 is connected to measurement unit 12. Measurement unit 12 is connected to control unit 13. Display unit 10 which displays the blood glucose level, temperature information reception unit 14 which receives temperature information from holder 2, and power supply 15 are also connected to control unit 13.

Barcode reading unit 64 which reads a barcode ID (individual identification information, and hereinafter, referred to as ID) of each of a measurer, a patient, and a bottle (not shown) accommodating a sensor is also connected to control unit 13.

Figure 5:
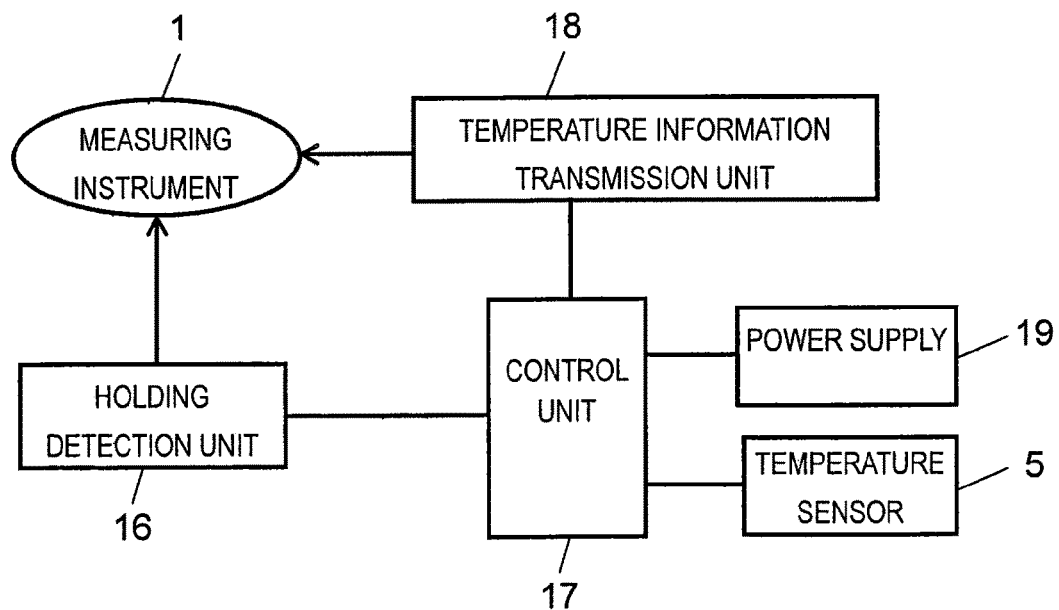
FIG. 5 is a functional block diagram of a temperature information supply instrument (holder) according to the first embodiment of the invention.

FIG. 5 is a functional block diagram of temperature information supply instrument (holder) 2 according to the first embodiment of the invention.

Holding detection unit 16 which detects measuring instrument 1 being held in holding portion 3 of holder 2 is connected to control unit 17. Temperature sensor 5 (see FIG. 1) arranged in the outer circumferential portion of holder 2, temperature information transmission unit 18 which sends a detected temperature detected by temperature sensor 5 to temperature information reception unit 14 of measuring instrument 1, and power supply 19 are also connected to control unit 17.

Returning to FIG. 2, description will be continued. In the holding state shown in FIG. 2, the end portion opposite to sensor mounting portion 9 of measuring instrument 1 comes into contact with stopper 4 and positioned. At this time, holding detection unit 16 provided on the surface of holding portion 3 of holder 2 is pressed by measuring instrument 1.

Accordingly, control unit 17 of holder 2 can detect measuring instrument 1 being held in holding portion 3. Holding detection unit 16 may be constituted by a general contact-type switch.

On the lower surface of measuring instrument 1, temperature information reception unit 14 having a metal terminal shape is provided. On the upper surface of holding portion 3, temperature information transmission unit 18 having a metal plate spring shape is provided. When measuring instrument 1 is held in holding portion 3, temperature information transmission unit 18 and temperature information reception unit 14 come into contact with each other, and mechanically and electrically connected together.

In the above-described configuration, the operation of biological sample measurement device 100 will be described as to a state of being used in a patient-room of a hospital.

Figure 6:
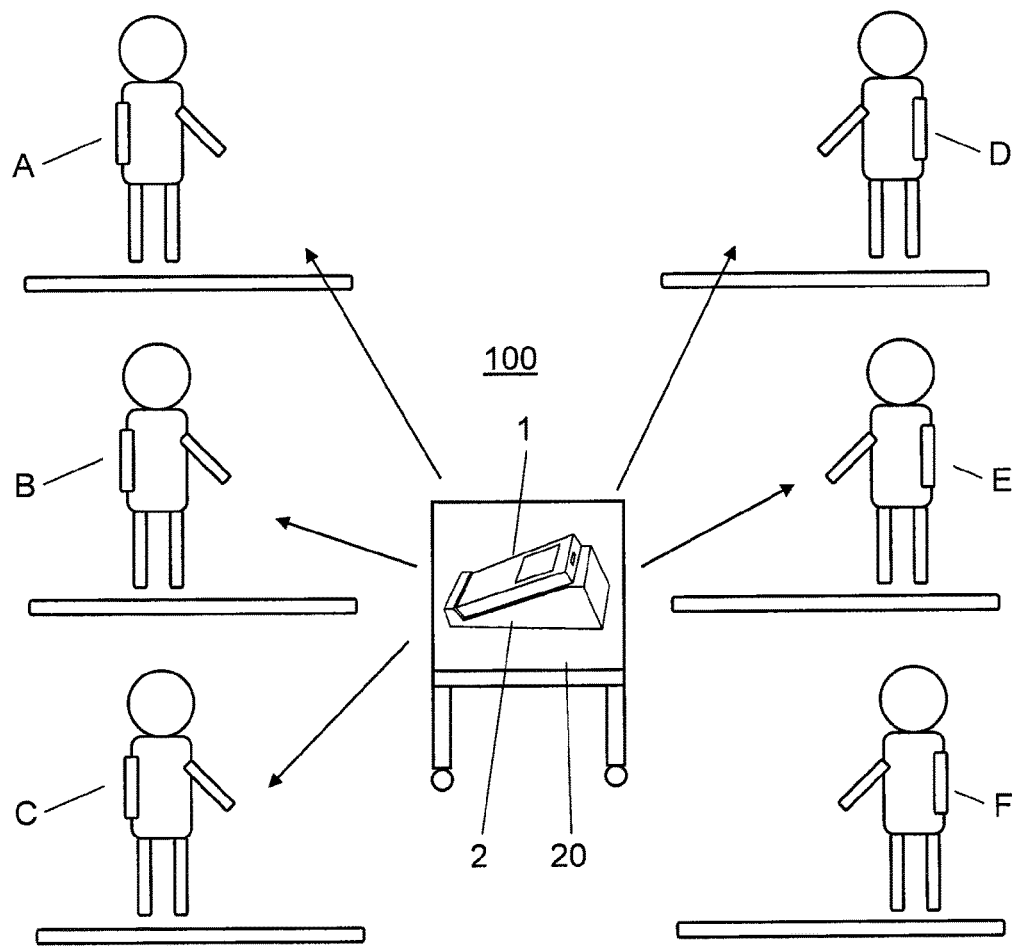
FIG. 6 is a diagram illustrating an example of a usage state of the biological sample measurement device according to the first embodiment of the invention.

FIG. 6 is a diagram showing an example of a usage state of biological sample measurement device 100 according to the first embodiment of the invention.

FIG. 6 shows a patient's room of a hospital. It is assumed that patients A to F are waiting in a patient's room with three people on the left side of the Figure and three people on the right side of the Figure, and they are partitioned by a curtain. A state where a measurer (for example, a nurse) moves wagon 20 with measuring instrument 1 and holder 2 thereon to the center portion of the patient's room is shown.

A case where the measurer sequentially measures the blood glucose levels of patients A to F using measuring instrument 1 in the above-described state will be described.

At the hospital, in order to keep a measurement record, for example, measurement-related information, such as a patient ID and a biological sample sensor ID, is collected for each measurement.

Hereinafter, for example, the measurement of the blood glucose level of patient A will be specifically described.

Figure 7:
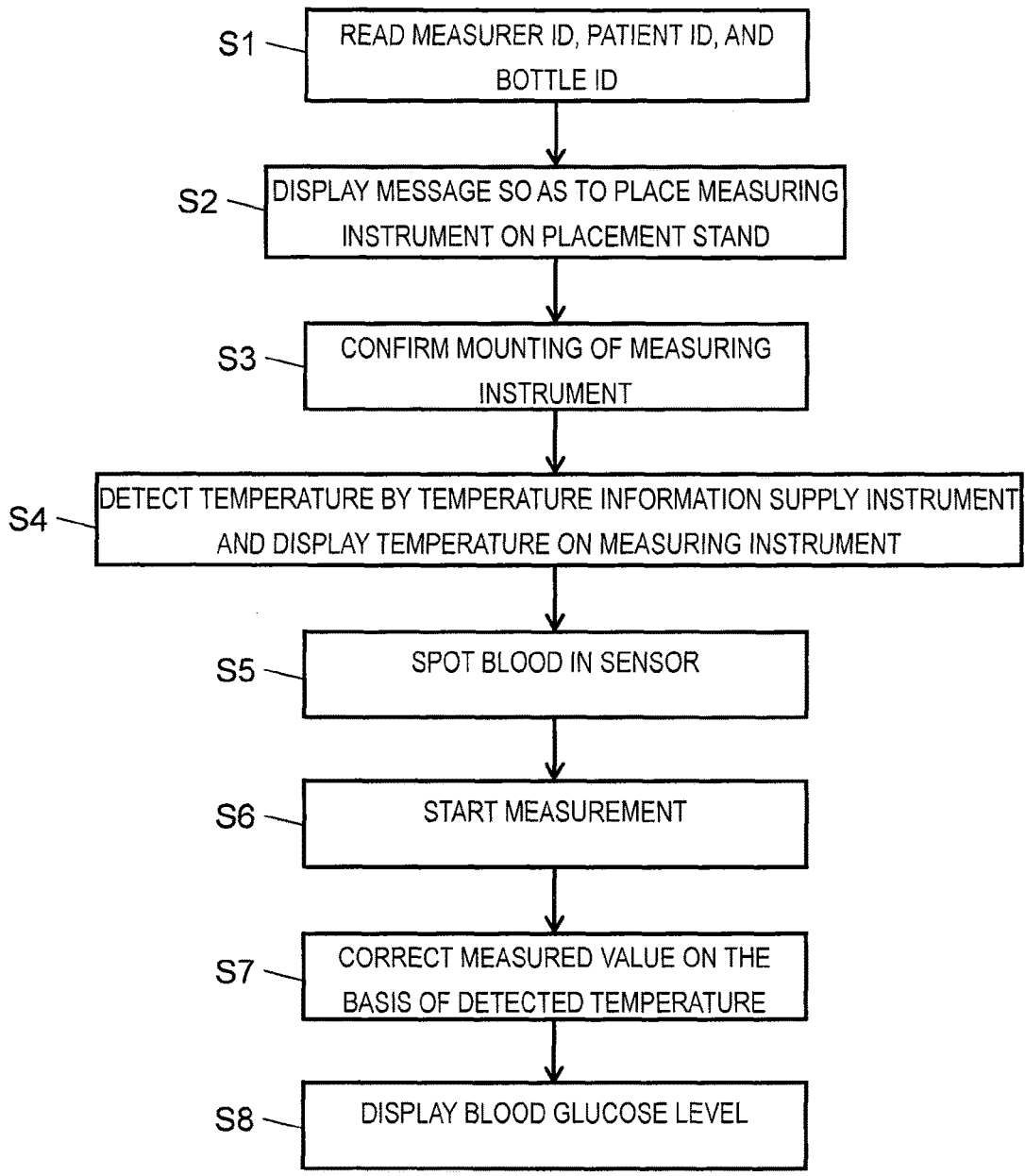
FIG. 7 is a flowchart showing an operation flow of the biological sample measurement device according to the first embodiment of the invention.
Figure 8A:
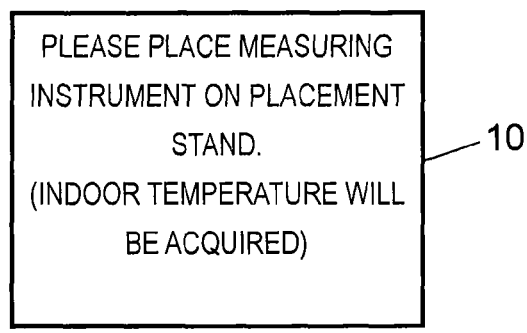
FIG. 8A is a diagram showing an example of a screen to be displayed on a display unit of the biological sample measuring instrument according to the first embodiment of the invention.
Figure 8B:
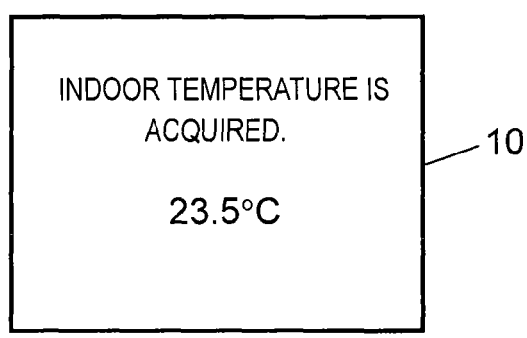
FIG. 8B is a diagram showing an example of a screen to be displayed on a display unit of the biological sample measuring instrument according to the first embodiment of the invention.

FIG. 7 is a flowchart showing an operation flow of biological sample measurement device 100 according to the first embodiment of the invention. FIGS. 8A and 8B are diagrams showing an example of a screen to be displayed on display unit 10 of biological sample measuring instrument 1 according to the first embodiment of the invention.

In regard to the measurement of the blood glucose level in a hospital service, for example, measurement-related information, such as a measurer ID, a patient ID, and a bottle ID with a sensor accommodated therein, is collected for each measurement. In order to perform the collection, the measurer pulls measuring instrument 1 out of holder 2, and reads the measurer ID, the patient ID, and the bottle ID using barcode reading unit 64 of measuring instrument 1 (S1).

At this time, a component (for example, a component, such as barcode reading unit 64, control unit 13, or display unit 10) embedded in measuring instrument 1 is operated. Accordingly, an increase in temperature occurs inside measuring instrument 1. However, since measuring instrument 1 is used in a state of being pulled out of holder 2, an increase in temperature inside measuring instrument 1 does not affect temperature sensor 5 of holder 2. That is, temperature sensor 5 of holder 2 can detect the temperature inside the patient's room as a measurement environment.

Next, the measurer mounts connection terminal 8 of blood glucose level sensor 7 in sensor mounting portion 9 so as to measure the blood glucose level of patient A. When this happens, power is supplied from power supply 15 to control unit 13 of measuring instrument 1. At this time, as shown in FIG. 8A, a message, "PLEASE PLACE MEASURING INSTRUMENT ON PLACEMENT STAND. (INDOOR TEMPERATURE WILL BE ACQUIRED)", is displayed on display unit 10 (S2).

The measurer who reads the message returns measuring instrument 1 to holder 2. The finger of patient A is stuck using a puncture tool (not shown). Then, as shown in FIG. 3, blood flows out slightly.

At this time, holder 2 detects measuring instrument 1 being held in holding portion 3 by holding detection unit 16. Holding detection unit 16 notifies control unit 17 of holding information (S3). A power switch (not shown) is provided in holder 2, and it is assumed that the power switch is turned on in advance, and power is supplied from power supply 19 to control unit 17.

Control unit 17 which is notified of the holding information detects the temperature inside the patient's room using temperature sensor 5. Control unit 17 transmits the detected temperature to measuring instrument 1 through temperature information transmission unit 18. Control unit 13 of measuring instrument 1 acquires the transmitted detected temperature through temperature information reception unit 14. Then, for example, as shown in FIG. 8B, a message, "INDOOR TEMPERATURE IS ACQUIRED. 23.5° C.", is displayed on display unit 10 (S4).

The operation of control unit 13 of measuring instrument 1 to receive the detected temperature from holder 2 is carried out during the stick operation of patient A.

Next, the measurer who ends the stick operation views the display of display unit 10 of measuring instrument 1 and confirms the acquired temperature of the patient's room. The measurer removes measuring instrument 1 from holder 2, and spots blood in spotting portion 11 at the leading end of blood glucose level sensor 7 (S5). In this way, the blood glucose level of patient A is measured by measurement unit 12 (S6).

Thereafter, control unit 13 corrects a measured value measured by measurement unit 12 on the basis of the detected temperature (measurement environmental temperature) detected by temperature sensor 5 of holder 2 (S7). Description as to the correction of the measured value based on the detected temperature will be omitted.

At this time, in this embodiment, the detected temperature by temperature sensor 5 of holder 2 provided outside measuring instrument 1 is used for the correction.

This point will be described in detail. As shown in FIG. 3, a reaction of blood glucose level measurement in blood glucose level sensor 7 is performed in spotting portion 11. That is, a reaction is performed at the measurement environmental temperature outside measuring instrument 1. Since the reaction fluctuates largely depending on the temperature, it is necessary to correct the measured value on the basis of the measurement environmental temperature.

In the related art, temperature sensor 5 is arranged inside measuring instrument 1. For this reason, an increase in temperature of a component (for example, a component, such as barcode reading unit 64, control unit 13, or display unit 10) mounted in measuring instrument 1 may affect the temperature to be detected by temperature sensor 5. As a result, the measured value may be corrected on the basis of a temperature different from the environmental temperature of spotting portion 11 of blood glucose level sensor 7 outside measuring instrument 1, and the measured value may vary.

There is also a method in which the measurement environmental temperature of spotting portion 11 outside measuring instrument 1 is estimated using the temperature to be detected by temperature sensor 5 and an increase in temperature of a component (for example, barcode reading unit 64, control unit 13, or display unit 10) embedded in measuring instrument 1. However, after all, the measured value may be corrected on the basis of a temperature different from the measurement environmental temperature of spotting portion 11, and the measured value may vary.

In contrast, in this embodiment, as described above, temperature sensor 5 is arranged in the outer circumferential portion of holder 2 provided separately from measuring instrument 1. For this reason, a temperature outside measuring instrument 1, that is, a temperature (measurement environmental temperature) corresponding to the environmental temperature of spotting portion 11 where a reaction of blood glucose level measurement is carried out can be measured and detected by temperature sensor 5. Control unit 13 corrects the blood glucose level of patient A on the basis of the measured measurement environmental temperature.

Accordingly, since it is possible to perform correction using temperature information corresponding to the measurement environment of spotting portion 11, it is possible to suppress variation in the measured value.

Control unit 13 displays the corrected blood glucose level on display unit 10, and the measurement of patient A ends (S8).

As described above, in Steps S1 to S8 of FIG. 7, when measuring instrument 1 acquires the measurement environmental temperature, it should suffice that measuring instrument 1 is put on holding portion 3 of holder 2. For this reason, it is possible to reduce the time for which measuring instrument 1 and holder 2 are in contact with each other, and heat inside measuring instrument 1 is not easily transmitted to temperature sensor 5.

In this embodiment, temperature sensor 5 is arranged in the outer circumferential portion near the bottom portion of holder 2. That is, temperature sensor 5 is arranged at a position as far as possible from measuring instrument 1 in a state of being put on holding portion 3 of holder 2. For this reason, even if measuring instrument 1 is put on holding portion 3 of holder 2, heat inside measuring instrument 1 is not easily transmitted to temperature sensor 5.

Thereafter, the measurer sequentially executes Steps S1 to S8 of FIG. 7 for patients B to F, and continuously performs the measurement of the blood glucose level. If the continuous measurement is performed, an increase in temperature due to electrical conduction is accumulated in a component (for example, barcode reading unit 64, control unit 13, or display unit 10) embedded in measuring instrument 1 and increases. During the continuous measurement, the measurer frequently grips measuring instrument 1. For this reason, heat of the hand of the measurer is transmitted to the inside of measuring instrument 1 and causes an increase in the internal temperature of measuring instrument 1.

However, in this embodiment, as described above, temperature sensor 5 is arranged in the outer circumferential portion of holder 2 provided separately from measuring instrument 1. For this reason, during the continuous measurement in the hospital service, a temperature corresponding to the measurement environmental temperature of spotting portion 11 can be measured and detected by temperature sensor 5 of holder 2. As a result, since it is possible to perform correction using temperature information corresponding to the measurement environment of spotting portion 11, it is possible to suppress variation in the measured value.

During the above-described continuous measurement, since the measurer does not grip holder 2, heat of the hand of the measurer is not transmitted to holder 2.

A case where temperature sensor 5 is provided in the outer circumferential surface of measuring instrument 1 and air outside a measurement location is measured may be considered. In this case, however, the hand of the measurer is likely to come into contact with temperature sensor 5, and it is not always possible to measure an appropriate temperature.

Second Embodiment

Next, a second embodiment of the invention will be described.

In a second embodiment, a configuration which is suitable for a measurement service in each of single occupant rooms of a hospital will be described. Biological sample measurement device 200 includes biological sample measuring instrument 22 and one or a plurality of temperature information supply instruments 21.

Figure 9:
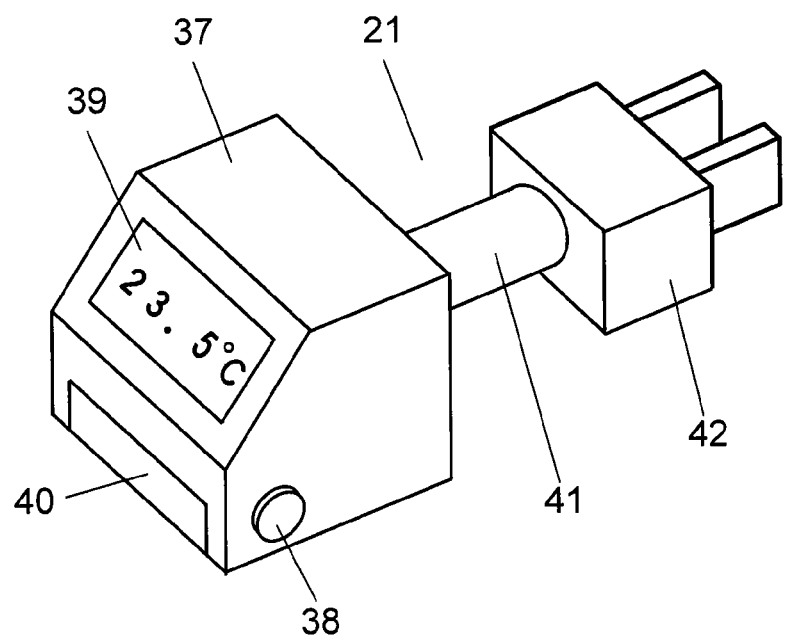
FIG. 9 is a perspective view showing the configuration of a temperature information supply instrument according to a second embodiment of the invention.
Figure 10:
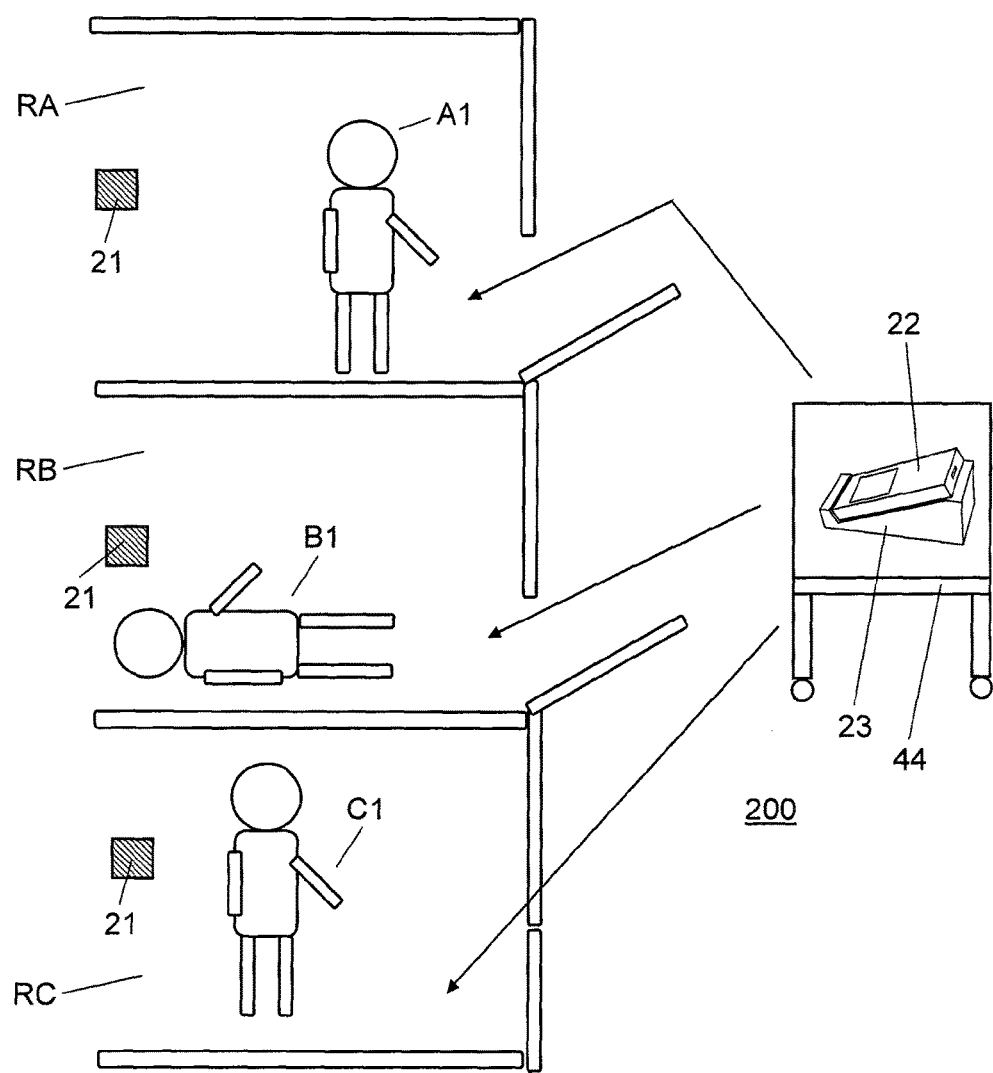
FIG. 10 is a diagram showing a usage environment of a temperature information supply instrument and a biological sample measuring instrument according to the second embodiment of the invention.

FIG. 9 is a perspective view showing the configuration of temperature information supply instrument 21 according to the second embodiment of the invention. FIG. 10 is a diagram showing the usage environment of temperature information supply instrument 21 and biological sample measuring instrument 22 according to the second embodiment of the invention.

In this embodiment, as shown in FIG. 10, the temperature information supply instrument 21 shown in FIG. 9 is arranged and used in each of single occupant rooms RA to RC of a hospital.

Figure 11:
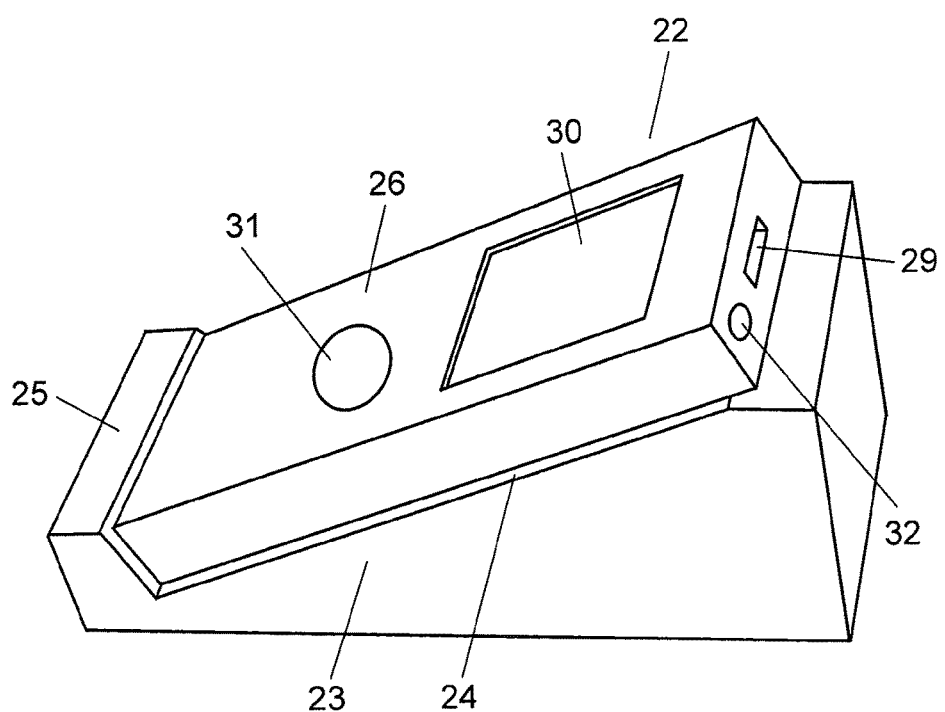
FIG. 11 is a perspective view showing the configuration of the biological sample measuring instrument according to the second embodiment of the invention.

FIG. 11 is a perspective view showing the configuration of biological sample measuring instrument 22 according to the second embodiment of the invention.

In FIG. 11, for example, biological sample measuring instrument (hereinafter, simply referred to as a measuring instrument) 22 measures the blood glucose level from blood. For example, when moving between patient's rooms at a hospital, measuring instrument 22 is held in holding portion 24 provided on the upper surface of holder 23.

As shown in FIG. 11, holding portion 24 has a surface which is inclined downward from the leading end to the rear end (from the right side to the left side when viewed toward the Figure). In the lower end portion of the inclination, stopper 25 which receives measuring instrument 22 in contact with the inclined surface of holding portion 24 is provided.

Figure 12:
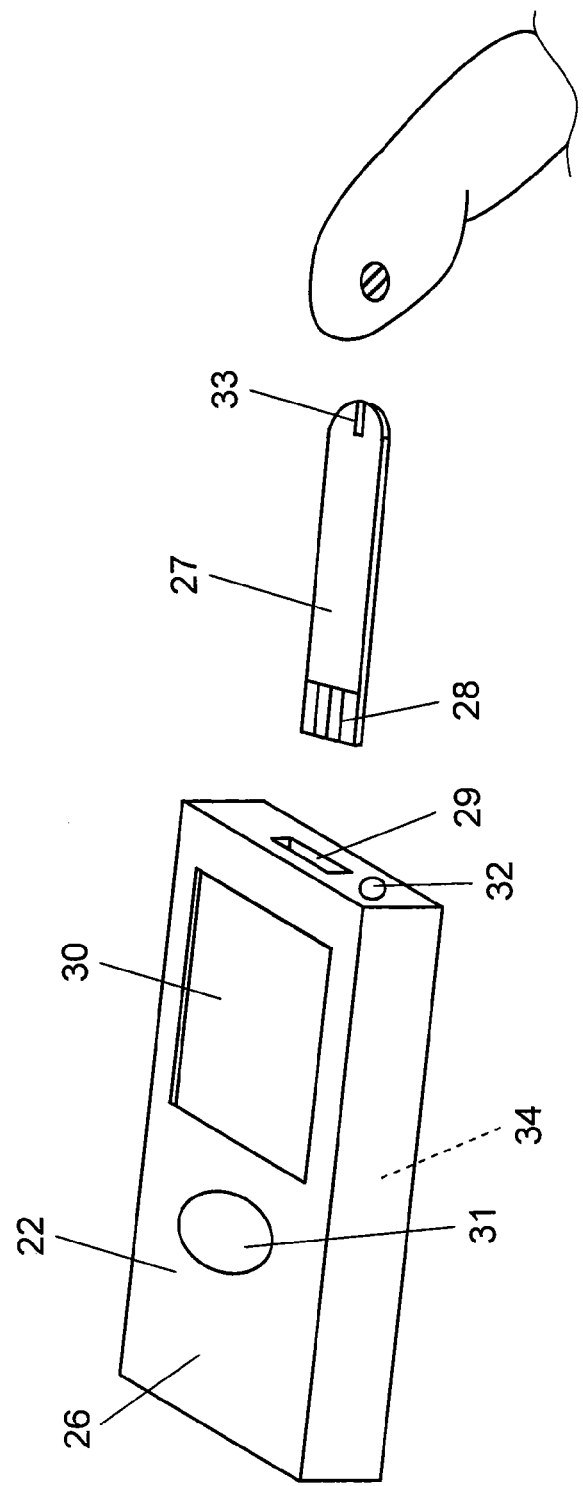
FIG. 12 is a perspective view showing the configuration of the biological sample measuring instrument according to the second embodiment of the invention.

FIG. 12 is a perspective view showing the configuration of biological sample measuring instrument 22 according to the second embodiment of the invention.

As shown in FIG. 12, measuring instrument 22 has plate-shaped main body case 26. In the leading end portion of main body case 26, sensor mounting portion 29 into which connection terminal 28 of thin plate-shaped blood glucose level sensor 27 is inserted is provided. On the upper surface of main body case 26, display unit 30 which displays the blood glucose level and temperature acquisition button 31 which inputs a trigger for acquiring temperature information from temperature information supply instrument 21 are provided.

In the leading end portion of main body case 26, temperature information reception unit 32 which performs communication by electric waves or light is provided so as to receive the temperature information from temperature information supply instrument 21. In this embodiment, it is assumed that temperature information reception unit 32 performs general infrared communication with temperature information transmission unit 40 of temperature information supply instrument 21.

The measurer mounts connection terminal 28 of blood glucose level sensor 27 in sensor mounting portion 29, and spots blood in spotting portion 33 at the leading end of blood glucose level sensor 27 in this state. Accordingly, the blood glucose level at this time is measured by measurement unit 34 embedded in main body case 26.

Figure 13:
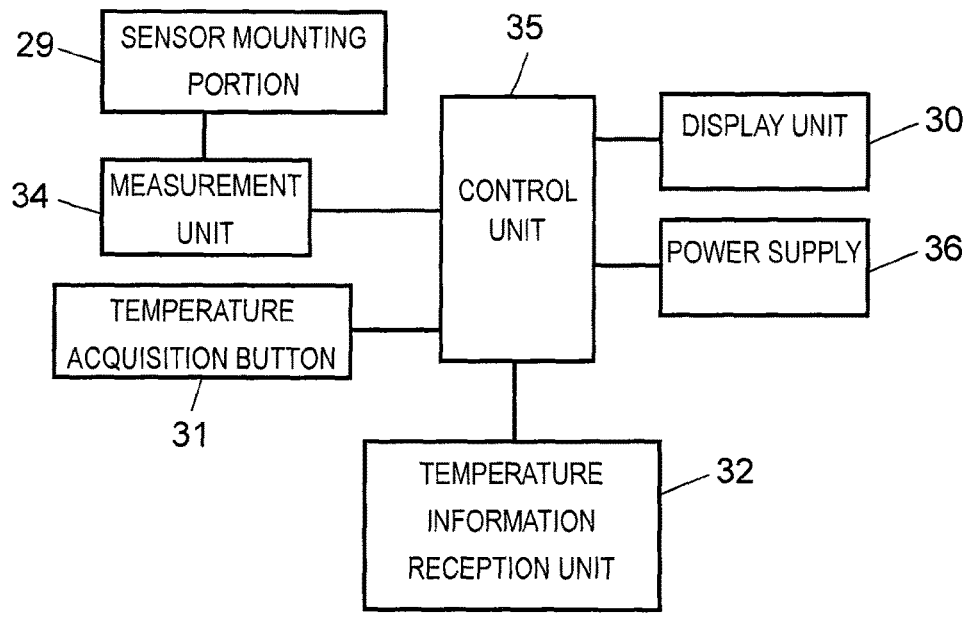
FIG. 13 is a functional block diagram of the biological sample measuring instrument according to the second embodiment of the invention.

FIG. 13 is a functional block diagram of biological sample measuring instrument 22 according to the second embodiment of the invention.

As shown in FIG. 13, sensor mounting portion 29 is connected to measurement unit 34. Measurement unit 34 is connected to control unit 35. Display unit 30 which displays the blood glucose level, temperature acquisition button 31, temperature information reception unit 32, and power supply 36 are also connected to control unit 35.

Returning to FIG. 9, the configuration of temperature information supply instrument 21 will be described. Temperature information supply instrument 21 has polyhedral main body case 37. In the outer circumferential portion of main body case 37, temperature sensor 38 which acquires a temperature outside temperature information supply instrument 21 is arranged. In an upper portion at the rear end (on the left side of FIG. 9) of main body case 37, display unit 39 which displays temperature information acquired by temperature sensor 38 is provided.

At the rear end of main body case 37, temperature information transmission unit 40 which performs communication with temperature information reception unit 32 of measuring instrument 22 by electric waves or light is provided. In this embodiment, temperature information transmission unit 40 performs general infrared communication with temperature information reception unit 32 of measuring instrument 22.

Power plug 42 is connected to the front end (on the right side of FIG. 9) of main body case 37 through connection portion 41. Power plug 42 is inserted into a general socket (for example, AC 100 V), and then power is supplied to temperature information supply instrument 21.

Figure 14:
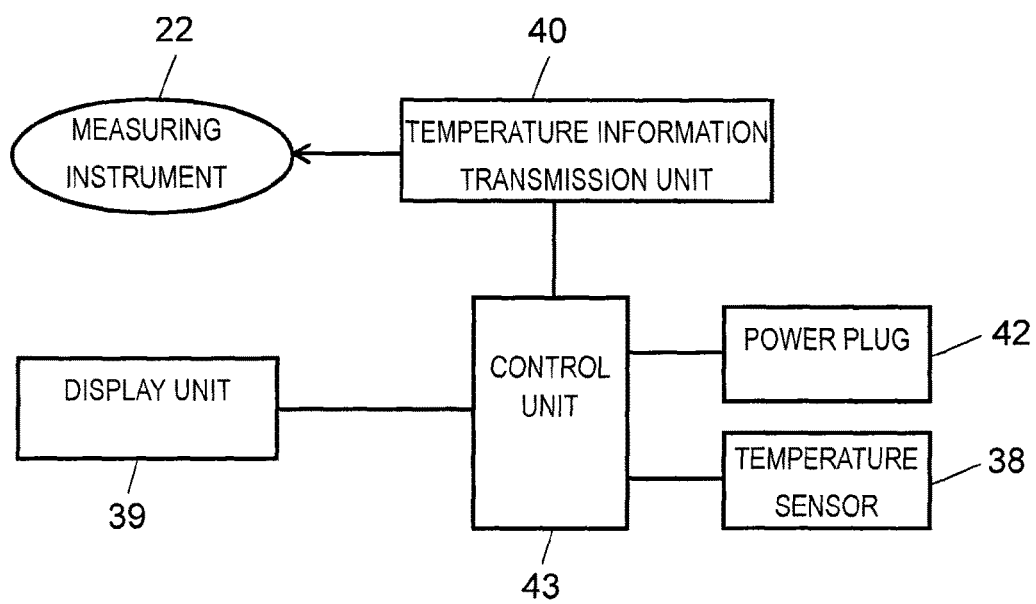
FIG. 14 is a functional block diagram of the temperature information supply instrument according to the second embodiment of the invention.

FIG. 14 is a functional block diagram of temperature information supply instrument 21 according to the second embodiment of the invention.

As shown in FIG. 14, temperature information transmission unit 40 which transmits the temperature information to measuring instrument 22 is connected to control unit 43. Display unit 39, temperature sensor 38, and power plug 42 are connected to control unit 43.

Hereinafter, the operations of biological sample measuring instrument 22 and temperature information supply instrument 21 in the above-described configuration will be described as to a state of being used in a hospital.

FIG. 10 shows a patient's room of a hospital. It is assumed that patients A1 to C1 are respectively waiting in single occupant rooms RA to RC of the patient's room. It is also assumed that the measurer puts measuring instrument 22 and holder 23 on wagon 44 so as to sequentially measure the blood glucose levels of patients A1 to C1.

In each of single occupant rooms RA to RC, power plug 42 of temperature information supply instrument 21 is inserted in advance into a socket which is prepared, for example, at a wall of a bed of each of single occupant rooms RA to RC. Temperature information supply instrument 21 is in an electric conduction state in a state of being attached to the wall. In this state, control unit 43 of temperature information supply instrument 21 regularly detects the indoor temperature of each of single occupant rooms RA to RC using temperature sensor 38 provided in the outer circumferential portion of main body case 37. The detected temperature is displayed on display unit 39 by control unit 43.

In this state, for example, the measurement of the blood glucose level of patient A1 will be described.

Figure 15:
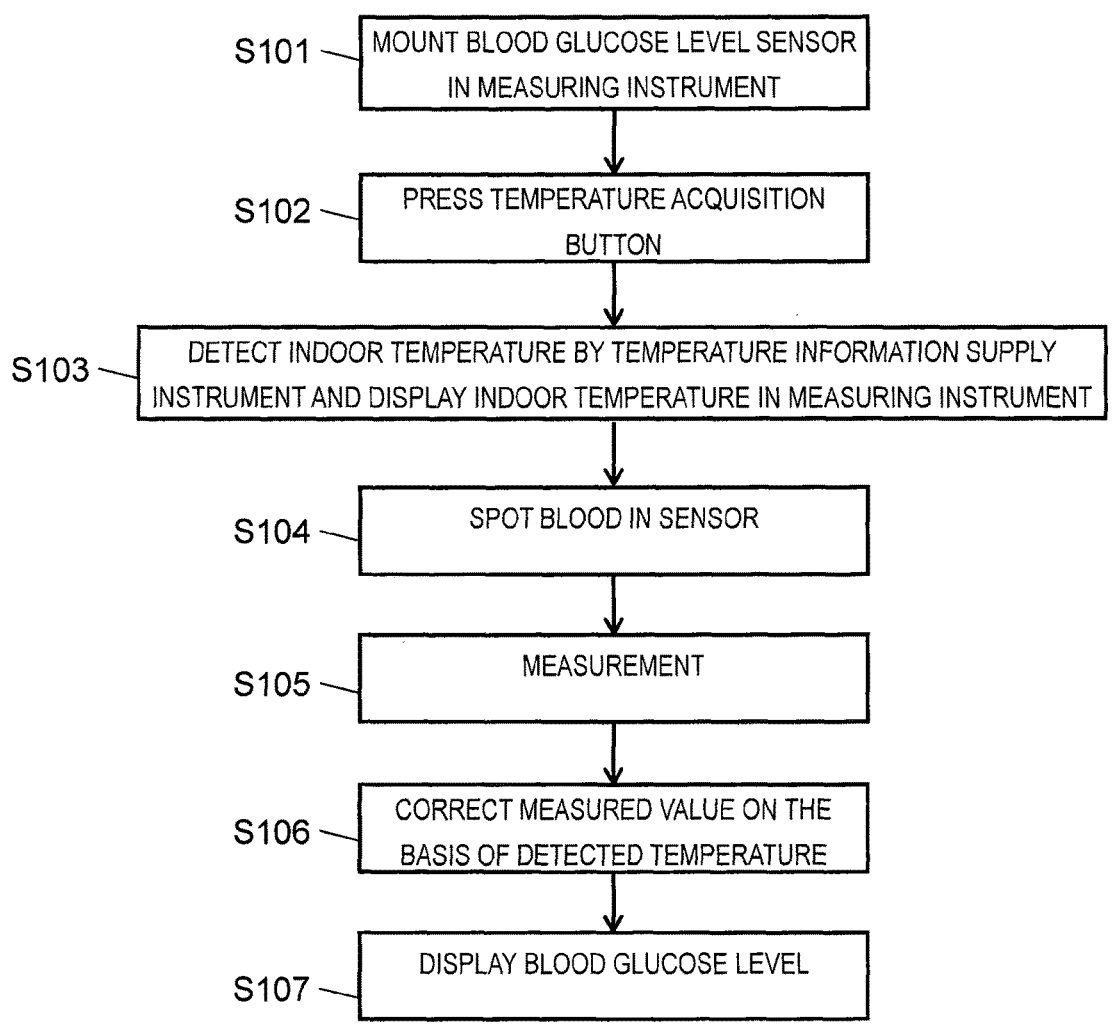
FIG. 15 is a flowchart showing an operation flow of a biological sample measurement device according to the second embodiment of the invention.
Figure 16A:
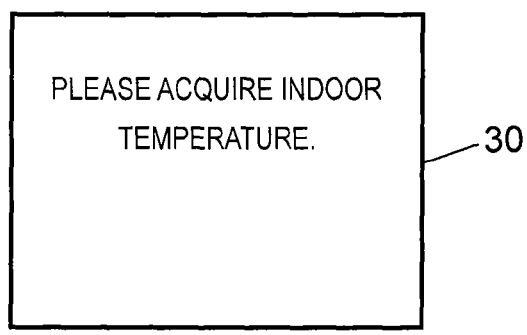
FIG. 16A is a diagram showing an example of a screen to be displayed on a display unit of the biological sample measuring instrument according to the second embodiment of the invention.
Figure 16B:
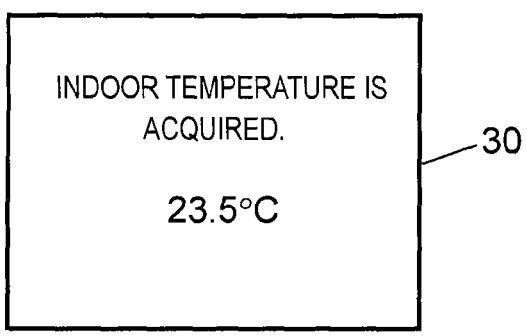
FIG. 16B is a diagram showing an example of a screen to be displayed on a display unit of the biological sample measuring instrument according to the second embodiment of the invention.

FIG. 15 is a flowchart showing an operation flow of biological sample measurement device 200 according to the second embodiment of the invention. FIGS. 16A and 16B are diagrams showing an example of a screen to be displayed on display unit 30 of biological sample measuring instrument 22 according to the second embodiment of the invention.

First, the measurer pushes wagon 44 and enters single occupant room RA of patient A1.

Next, the measurer takes measuring instrument 22 from holder 23, and as shown in FIG. 12, mounts connection terminal 28 of blood glucose level sensor 27 in sensor mounting portion 29. Accordingly, power is supplied from power supply 36 to control unit 35 of measuring instrument 22, and then, as shown in FIG. 16A, a message, "PLEASE ACQUIRE INDOOR TEMPERATURE", is displayed on display unit 30 (S101).

The measurer who reads the message turns temperature information reception unit 32 in the leading end portion of measuring instrument 22 toward temperature information transmission unit 40 of temperature information supply instrument 21 provided at the wall of the bed, and presses temperature acquisition button 31 (see FIG. 12) of measuring instrument 22 (S102).

Accordingly, a temperature acquisition request is transmitted from temperature information reception unit 32 to temperature information transmission unit 40. Control unit 43 of temperature information supply instrument 21 receives the temperature acquisition request through temperature information transmission unit 40. Control unit 43 detects the indoor temperature inside single occupant room RA using temperature sensor 38 and displays the indoor temperature on display unit 39.

Control unit 43 transmits temperature information regarding the detected temperature (indoor temperature, that is, measurement environmental temperature) in single occupant room RA from temperature information transmission unit 40 to temperature information reception unit 32 of measuring instrument 22. On measuring instrument 22 side, control unit 35 receives the temperature information through temperature information reception unit 32, and for example, as shown in FIG. 16B, "INDOOR TEMPERATURE IS ACQUIRED. 23.5° C." is displayed on display unit 30 (S103).

The measurer views the display and the temperature displayed on display unit 39 of temperature information supply instrument 21, and can confirm whether or not the indoor temperature can be acquired correctly.

Thereafter, the measurer takes a puncture tool (not shown), sticks the finger of patient A1 to flow out blood. As shown in FIG. 12, the measurer spots blood in spotting portion 33 at the leading end of blood glucose level sensor 27 (S104). Accordingly, the blood glucose level of patient A1 is measured by measurement unit 34 (S105).

Thereafter, control unit 35 corrects the measured value measured by measurement unit 34 on the basis of the detected temperature (measurement environmental temperature) detected by temperature sensor 38 of temperature information supply instrument 21 (S106).

In this way, in this embodiment, the detected temperature by temperature sensor 38 of temperature information supply instrument 21 provided separately from measuring instrument 22 is used for the correction of the measured value.

This point will be described in detail. As shown in FIG. 12, a reaction of blood glucose level measurement in blood glucose level sensor 27 is performed in spotting portion 33. That is, the reaction is performed at the measurement environmental temperature (indoor temperature) outside measuring instrument 22. Since the reaction fluctuates largely depending on the temperature, it is necessary to correct the measured value on the basis of the measurement environmental temperature.

The measurement environmental temperature which is used for correction is acquired by temperature sensor 38.

In the related art, temperature sensor 38 is arranged inside measuring instrument 22. For this reason, an increase in temperature of a component (for example, a component, such as control unit 35 or display unit 30) embedded in measuring instrument 22 may affect the temperature to be detected by temperature sensor 38. As a result, the measured value may be corrected on the basis of a temperature different from the environmental temperature of spotting portion 33 of blood glucose level sensor 27 outside measuring instrument 22, and in this case, the measured value may vary.

There is also a method in which the measurement environmental temperature of spotting portion 33 outside measuring instrument 22 is estimated using the temperature to be detected by temperature sensor 38 and an increase in temperature of a component (for example, control unit 35, display unit 30, or the like) embedded in measuring instrument 22. However, after all, the measured value may be corrected on the basis of a temperature different from the measurement environmental temperature of spotting portion 33, and the measured value may vary.

In contrast, in this embodiment, as described above, temperature sensor 38 is arranged in the outer circumferential portion of temperature information supply instrument 21 provided separately from measuring instrument 22. For this reason, temperature outside measuring instrument 22, that is, the measurement environmental temperature (indoor temperature) of spotting portion 33 where a reaction of blood glucose level measurement is carried out can be measured and detected by temperature sensor 38. Control unit 35 corrects the blood glucose level of patient A1 on the basis of the measured environmental temperature.

Accordingly, since it is possible to perform correction using temperature information corresponding to the measurement environment of spotting portion 33, it is possible to suppress variation in the measured value.

Control unit 35 displays the corrected blood glucose level on display unit 30, and the measurement of patient A1 ends (S107).

Thereafter, the measurer pushes wagon 44, as shown in FIG. 10, sequentially visits single occupant rooms RB and RC of patients B1 and C1, and performs a measurement.

At this time, the air conditioner may be adjusted in each of single occupant rooms RA to RC. For example, the indoor temperature of single occupant room RA may be set to be higher than a designated temperature, and the indoor temperature of single occupant room RB may be set to be lower than the designated temperature. For this reason, a difference in temperature of several degrees is generated between the indoor temperature of single occupant room RA and the indoor temperature of single occupant room RB.

Even in this case, in this embodiment, since temperature information supply instrument 21 is arranged in advance in each of single occupant rooms RA to RC in an electrical conduction state, it is possible to detect an accurate indoor temperature.

After moving from single occupant room RA to single occupant room RB, as described above, measurer mounts connection terminal 28 of blood glucose level sensor 27 in sensor mounting portion 29, spots blood in spotting portion 33 at the leading end of blood glucose level sensor 27 in this state, and measures the blood glucose level. As shown in FIG. 12, blood glucose level sensor 27 which is used at this time has a thin plate shape. For this reason, when moving from single occupant room RA to single occupant room RB, even if there is a difference in temperature of, for example, several degrees between both single occupant rooms, thin plate-shaped blood glucose level sensor 27 has a large surface area with respect to volume and thus readily reaches the same temperature as the indoor temperature of single occupant room RB as a moving destination.

Thereafter, the indoor temperature of single occupant room RB, that is, a temperature corresponding to the measurement environmental temperature of spotting portion 33 is measured and detected by temperature sensor 38 arranged in the outer circumferential portion of temperature information supply instrument 21. Measuring instrument 22 corrects the blood glucose level of patient B1 using the measured measurement environmental temperature. Accordingly, it is possible to suppress variation in the measured value.

A case where temperature sensor 38 is provided in the outer circumferential surface of measuring instrument 22, and air outside a measurement location is measured may be considered. When this happens, however, the hand of the measurer is likely to come into contact with temperature sensor 38, and it is not always possible to measure an appropriate temperature.

Although in this embodiment, a configuration in which temperature information transmission unit 40 performs general infrared communication is made, a configuration in which electric-wave communication is performed may be made. When electric-wave communication is used, the transmission/reception distance is shortened, thereby preventing interference of temperature information of adjacent rooms.

Third Embodiment

Next, a third embodiment of the invention will be described.

Figure 17:
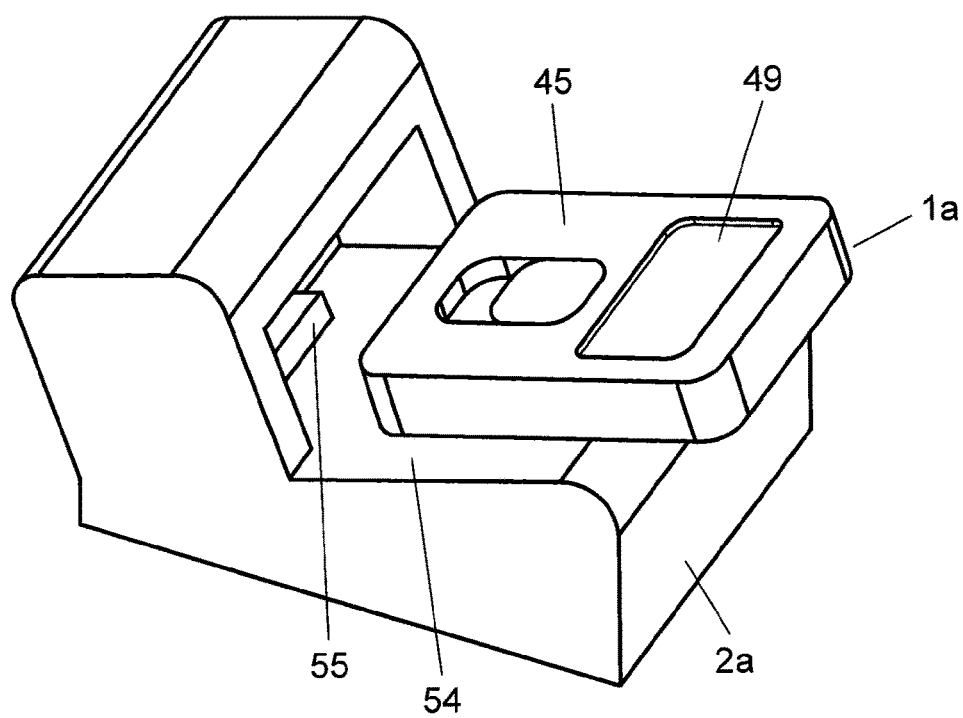
FIG. 17 is a perspective view showing the configuration of a biological sample measurement device according to a third embodiment of the invention.
Figure 18:
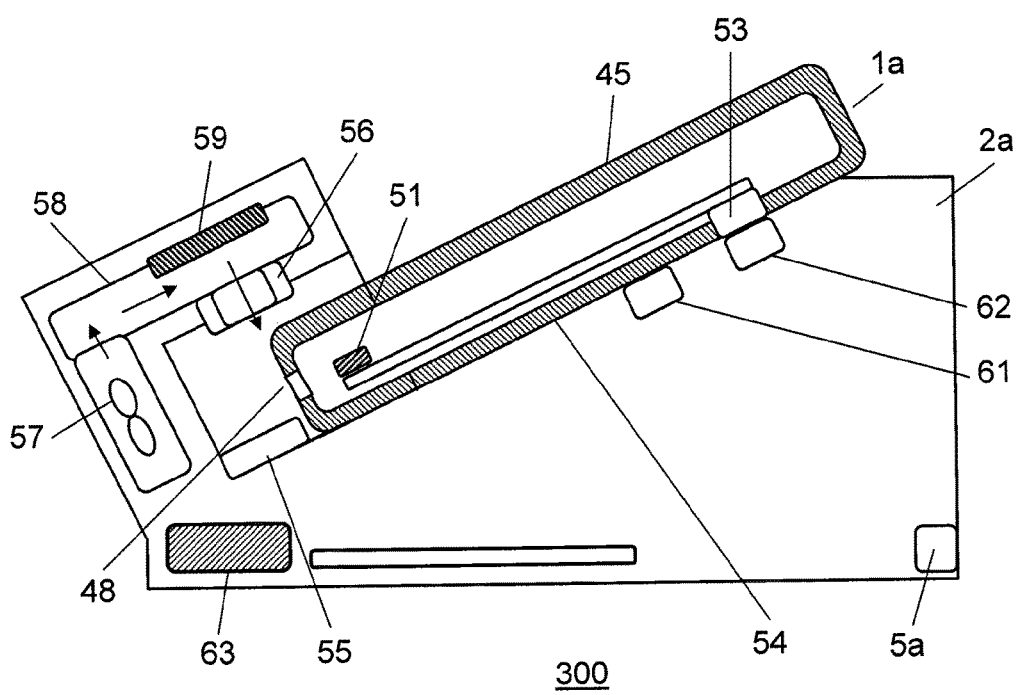
FIG. 18 is a diagram showing the sectional configuration of the biological sample measurement device according to the third embodiment of the invention.
Figure 19:
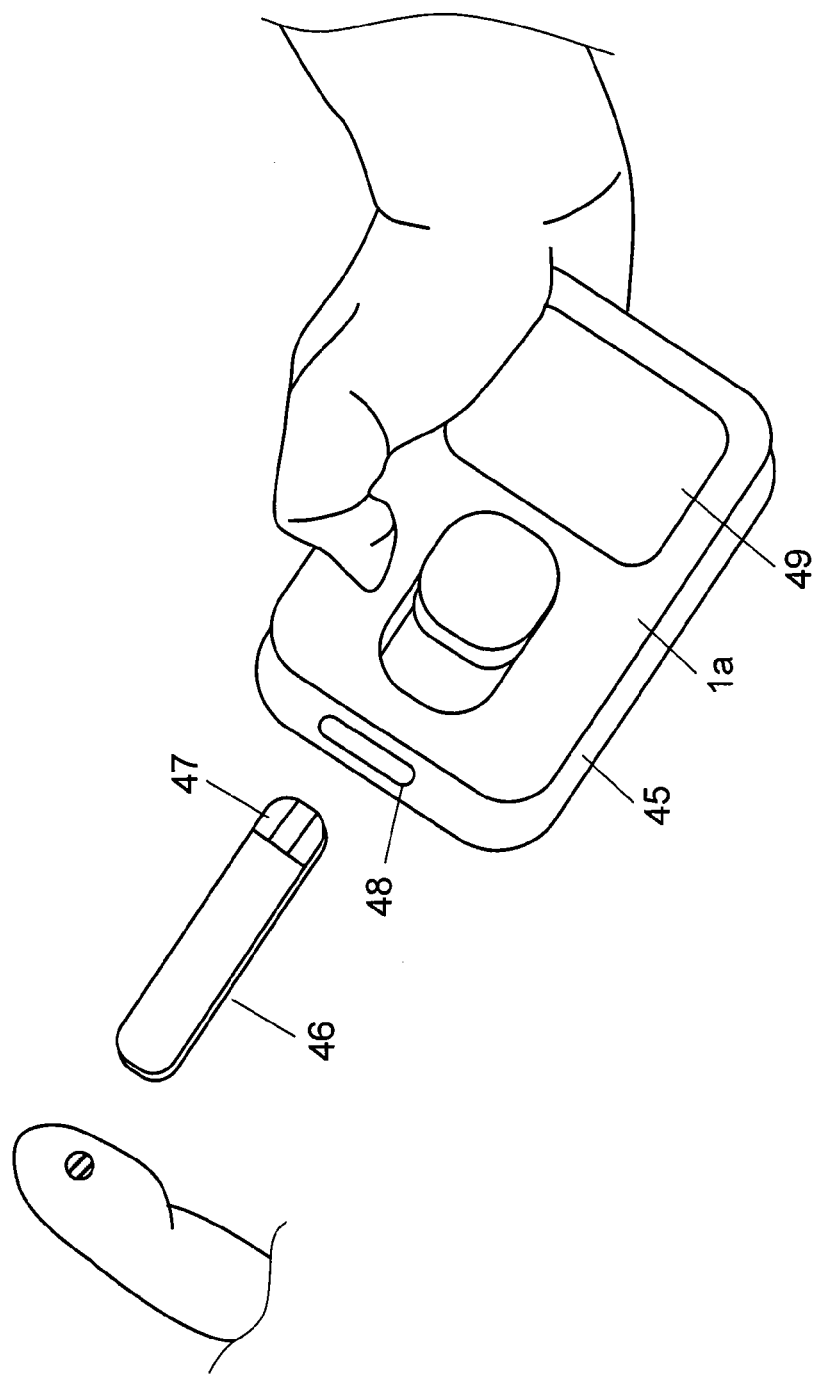
FIG. 19 is a perspective view showing the configuration of a biological sample measuring instrument according to the third embodiment of the invention.

FIG. 17 is a perspective view showing the configuration of biological sample measurement device 300 according to a third embodiment of the invention. FIG. 18 is a diagram showing the sectional configuration of biological sample measurement device 300. FIG. 19 is a perspective view showing the configuration of biological sample measuring instrument 1a according to the third embodiment of the invention.

As shown in FIG. 17, biological sample measurement device 300 has biological sample measuring instrument (referred to as measuring instrument) 1a and temperature information supply instrument (referred to as a holder) 2a.

Biological sample measurement device 300 of this embodiment also meets an urgent measurement need in a hospital. For example, at a hospital, for a patient who is urgently transported, it is necessary to perform an urgent measurement using measuring instrument 1a at a location away from holder 2a. At the time of this urgent measurement, there is a case where measuring instrument 1a may not acquire temperature information from temperature sensor 5a (first temperature sensor, see FIG. 18) of holder 2a.

For this reason, in this embodiment, temperature sensor 51 (second temperature sensor) is provided inside measuring instrument 1a. Holder 2a has fan 57 (see FIG. 18) which blows air to measuring instrument 1a.

During an urgent measurement, measuring instrument 1a acquires temperature information from temperature sensor 51 provided therein and corrects the measured value. After the urgent measurement, if the measurer holds measuring instrument 1a in holder 2a, fan 57 of holder 2a cools temperature sensor 51 of measuring instrument 1a to the indoor temperature.

Accordingly, even when an urgent measurement is required again, since measuring instrument 1a can acquire accurate temperature information (indoor temperature, that is, measurement environmental temperature) from temperature sensor 51, it is possible to suppress variation in the measured value.

Hereinafter, description will be provided in detail.

In FIGS. 17 and 18, for example, measuring instrument 1a measures the blood glucose level from blood. Other than a measurement, for example, during moving between patient's rooms or the like, as shown in FIG. 18, measuring instrument 1a is detachably held in holder 2a.

As shown in FIG. 19, measuring instrument 1a has plate-shaped main body case 45. In the leading end portion of main body case 45, opening 48 into which terminal portion 47 of thin plate-shaped blood glucose level sensor (an example of a biological sample measurement sensor) 46 is inserted is provided. On the upper surface of main body case 45, display unit 49 which displays the blood glucose level is provided.

If the measurer attaches blood to a detection unit (not shown) in the leading end portion of blood glucose level sensor 46 in a state where terminal portion 47 of blood glucose level sensor 46 is inserted into opening 48, the blood glucose level at this time is measured by measurement unit 50 (see FIG. 20) embedded in main body case 45.

Figure 20:
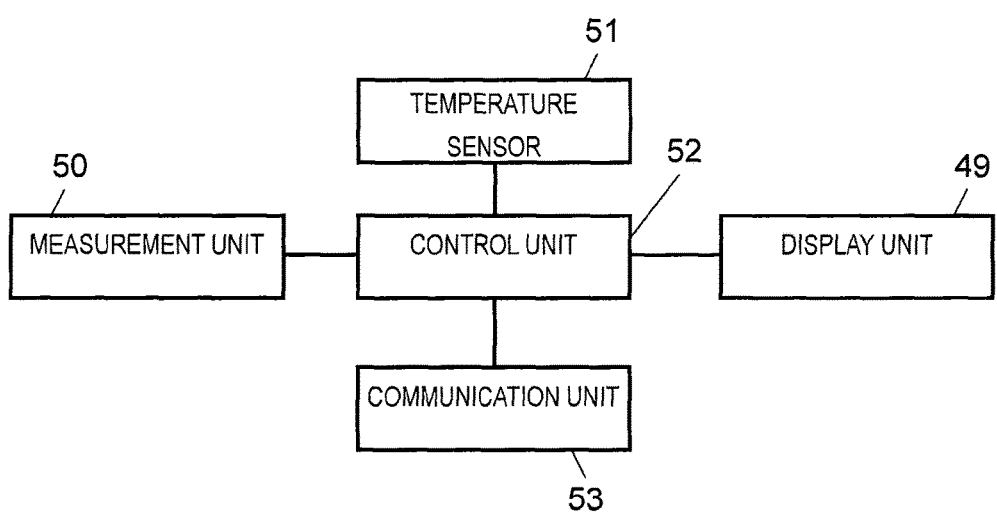
FIG. 20 is a functional block diagram of the biological sample measuring instrument according to the third embodiment of the invention.

FIG. 20 is a functional block diagram of biological sample measuring instrument 1a according to the third embodiment of the invention.

As shown in FIG. 20, communication unit 53, measurement unit 50, display unit 49, and temperature sensor 51 are connected to control unit 52.

As described above, at a hospital, for example, only measuring instrument 1a is taken from holder 2a and an urgent measurement is performed, for example, for a patient who is urgently transported.

During this urgent measurement, instead of acquiring the temperature from holder 2a, temperature information is acquired by temperature sensor 51 (see FIG. 18) provided near opening 48 inside main body case 45.

Specifically, if the measurer presses an urgent measurement button (not shown), control unit 52 acquires the temperature information from temperature sensor 51, and the measured value is corrected on the basis of the temperature information. Then, the corrected blood glucose level is displayed on display unit 49.

During the urgent measurement, since it should suffice that only the blood glucose level may be measured, collection of measurement-related information, that is, the measurer ID, the patient ID, the bottle ID, and the like using a barcode reading unit (not shown) of measuring instrument 1a may not be read.

After the urgent measurement ends, the measurer brings back measuring instrument 1a to the location of holder 2a, and as shown in FIG. 18, holds measuring instrument 1a in holder 2a. As shown in FIGS. 17 and 18, holder 2a is provided with holding portion 54, which is inclined downward from one end to the other end (from the right side to the left side when viewed toward the Figures), on the upper surface thereof. At the lower end of the inclination, stopper 55 which receives measuring instrument 1a in contact with the inclined surface of holding portion 54 is provided.

As shown in FIG. 18, opening 48 side of measuring instrument 1a comes into contact with stopper 55 and is positioned. In this state, air is blown from upper vent 56, thereby cooling opening 48 side of main body case 45 of measuring instrument 1a, that is, the side on which temperature sensor 51 is provided inside main body case 45, and cooling the inside of main body case 45 through opening 48.

Holder 2a is provided with fan 57. Fan 57 and vent 56 are connected by air duct 58. Inside air duct 58, sterilizer 59 which generates OH radical or active oxygen is arranged.

As shown in FIG. 19, a state where the measurement of the blood glucose level is completed, and as shown in FIG. 18, main body case 45 with blood glucose level sensor 46 extracted from opening 48 is held in holding portion 54 of holder 2a is assumed. In this state, measuring instrument 1a is cooled by air (air inside or outside the room as a measurement location) blown from fan 57 through air duct 58 and vent 56. Accordingly, the detected temperature by temperature sensor 51 represents a value approximated to the temperature of the measurement location. Therefore, temperature correction which is performed in control unit 52 is performed appropriately.

Figure 21:
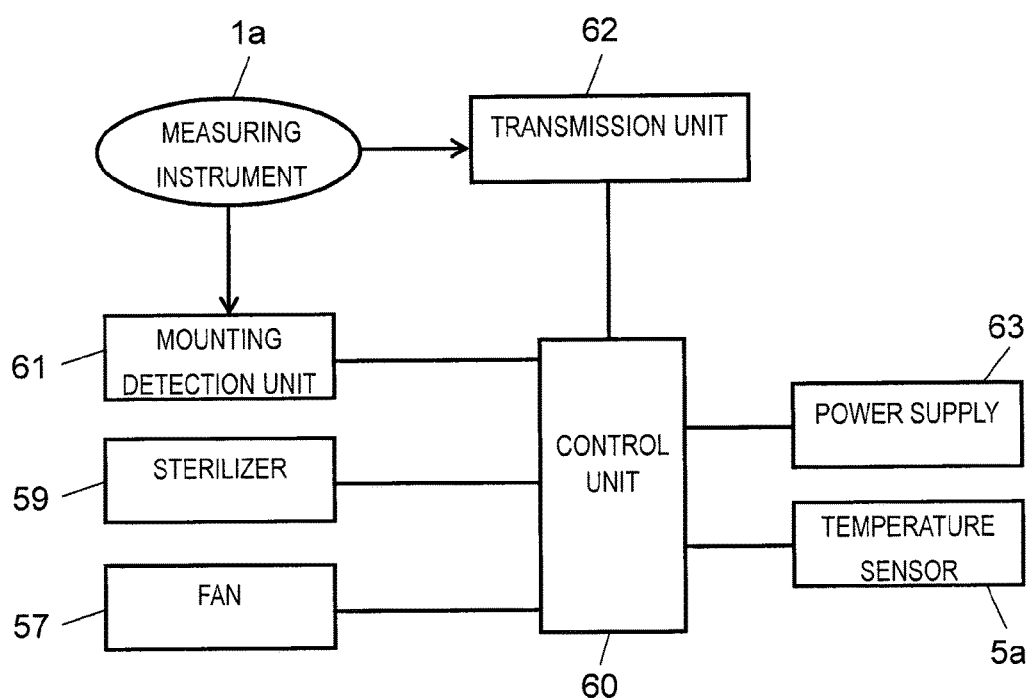
FIG. 21 is a functional block diagram of the temperature information supply instrument according to the third embodiment of the invention.

FIG. 21 is a functional block diagram of holder 2a according to the third embodiment of the invention.

As shown in FIG. 21, fan 57 and sterilizer 59 are connected to control unit 60 (second control unit). Control unit 60 is connected to temperature sensor 5a which detects a temperature (measurement environmental temperature) of a measurement location, mounting detection unit 61 which detects measuring instrument 1a being mounted in holding portion 54 of holder 2a, communication unit 62 which performs infrared communication with communication unit 53 of measuring instrument 1a, and power supply 63.

In the above-described configuration, as shown in FIG. 19, a case where the measurement of the blood glucose level is completed, and as shown in FIG. 18, main body case 45 with blood glucose level sensor 46 extracted from opening 48 is held in holding portion 54 of holder 2a is assumed.

Figure 22:
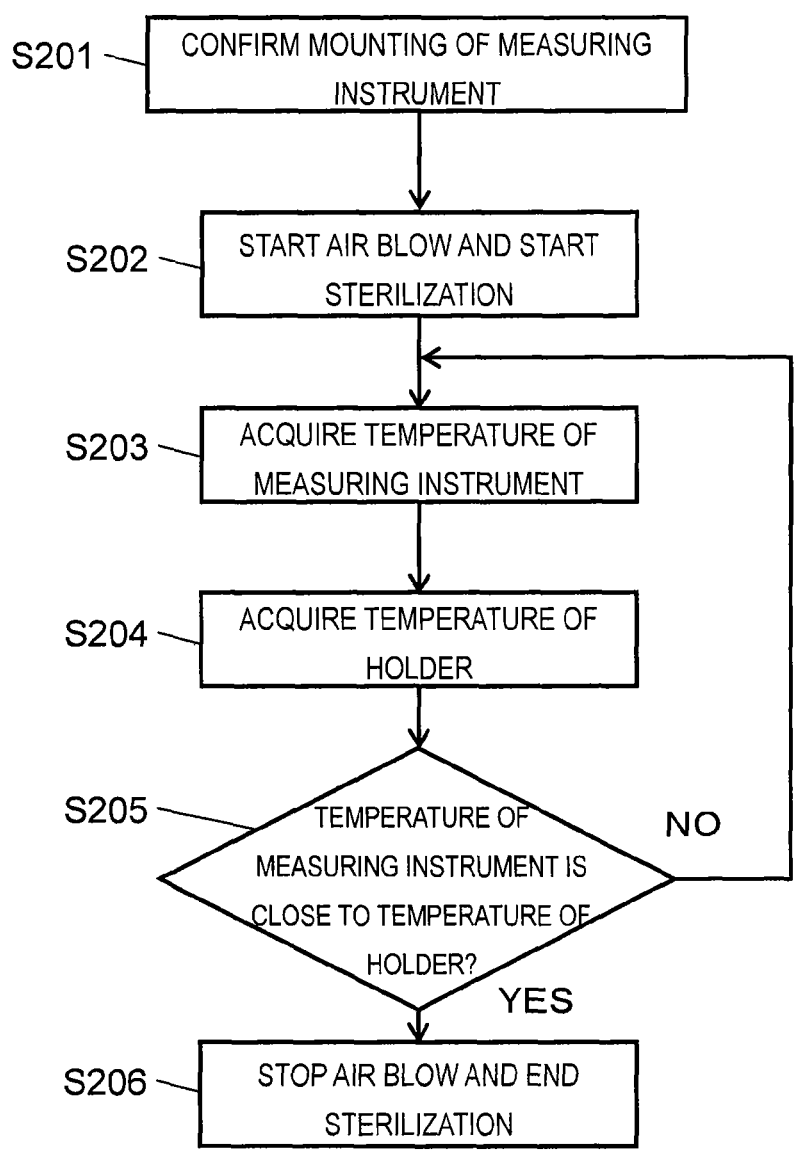
FIG. 22 is a flowchart showing an operation flow of the biological sample measurement device according to the third embodiment of the invention.

FIG. 22 is a flowchart showing an operation flow of biological sample measurement device 300 according to the third embodiment of the invention.

In the above-described state, the mounting of measuring instrument 1a is detected by mounting detection unit 61 (S201).

Accordingly, fan 57 and sterilizer 59 are driven by control unit 60 of holder 2a (S202). Accordingly, air starts to blow from fan 57 to the portion of opening 48 of main body case 45 through air duct 58 and vent 56, and cooling starts from the portion of opening 48.

Simultaneously, sterilization near opening 48 is performed using OH radical or active oxygen generated by sterilizer 59. When cooling near opening 48 is performed, temperature information regarding the detected temperature from temperature sensor 51 of measuring instrument 1a is supplied to control unit 60 through communication unit 53 and communication unit 62. The detected temperature from temperature sensor 5a of holder 2a is supplied to control unit 60 (S203 and S204).

Control unit 60 of holder 2a compares the detected temperature detected by temperature sensor 51 of measuring instrument 1a with the detected temperature detected by temperature sensor 5a of holder 2a. Control unit 60 continues air blow and sterilization until the detected temperature of temperature sensor 51 of measuring instrument 1a is close to a set temperature set near the detected temperature of temperature sensor 5a of holder 2a (S205). Thereafter, if the set temperature is reached, control unit 60 stops the driving of fan 57 and sterilizer 59 (S206).

At this time, as shown in FIG. 18, air from vent 56 is blown into main body case 45 through opening 48 of main body case 45. With the air blow, the inside of main body case 45 can be cooled directly. As a result, the inside of main body case 45 can be cooled quickly. For this reason, there is no case where the temperature in main body case 45 increases largely compared to the temperature inside the room as the measurement location or an outdoor temperature.

As a result, for example, during an urgent measurement or the like, when the measured value of measurement unit 50 is corrected on the basis of the detected temperature detected by temperature sensor 51 in main body case 45, it is possible to reduce a measurement error.

When the power supply of measuring instrument 1a is constituted by a rechargeable battery, for example, if a charging unit is provided in holder 2a, and measuring instrument 1a is held in holder 2a, charging of the rechargeable battery can be performed. However, during charging, the rechargeable battery is heated due to charging, and the internal temperature of main body case 45 is likely to increase.

Even in this case, according to this embodiment, since cooling by fan 57 of holder 2a is performed in a state where measuring instrument 1a is held in holder 2a, there is no case where the temperature inside main body case 45 of measuring instrument 1a increases largely from the temperature inside or outside the room as the measurement location.

As a result, when the measured value of measurement unit 50 is corrected on the basis of the detected temperature detected by temperature sensor 51 in main body case 45, it is possible to reduce a measurement error.

As described above, in this embodiment, measuring instrument 1a is held in holder 2a, and cooled by fan 57 such that the temperature inside measuring instrument 1a becomes the indoor temperature.

At this time, as shown in FIGS. 17 and 18, fan 57, vent 56, and air duct 58 constituting a cooling mechanism is provided at the rear end of holder 2a, and covers opening 48 of main body case 45 of measuring instrument 1a. Meanwhile, a portion from the central portion to the leading end portion of measuring instrument 1a is not covered with the cooling mechanism of holder 2a and is in an open state.

For this reason, when the measurer takes measuring instrument 1a from holder 2a, for example, the measurer can grip the middle portion of measuring instrument 1a using his/her thumb and forefinger. Accordingly, measuring instrument 1a can be easily taken from holder 2a.

In this embodiment, the urgent measurement has been taken as an example, and the measurement when measuring instrument 1a cannot receive the temperature information from temperature sensor 5a of holder 2a has been described. Meanwhile, during a normal measurement, similarly to the description in the first embodiment and the second embodiment, measuring instrument 1a receives the temperature information (measurement environmental temperature) of temperature sensor 5a of holder 2a through communication unit 62 of holder 2a and communication unit 53 of measuring instrument 1a, and corrects the measured value on the basis of the received temperature information.

Although in the respective embodiments, an example where the biological sample measurement device measures the blood glucose level of a human body has been described, the invention is not limited to this example. The biological sample measurement device includes a device which measures various biological samples undergoing variation in a measured value depending on change in temperature of a measurement environment.

INDUSTRIAL APPLICABILITY

As described above, according to the invention, since it is possible to exhibit a special effect of suppressing variation in the measured value, the invention is useful as a biological sample measurement device including a biological sample measuring instrument and a temperature information supply instrument supplying temperature information to the biological sample measuring instrument, or the like.

The invention claimed is:
1. A biological information measurement method used in a biological sample measurement device,
   wherein the biological sample measurement device comprises:
   a biological sample measuring instrument; and
   a first temperature information supply instrument which supplies temperature information regarding a measurement environment to the biological sample measuring instrument,
   the biological sample measuring instrument has
      a measurement unit which measures a biological sample spotted in a biological sample measurement sensor, the biological sample measurement sensor being a separate component from the first temperature information supply instrument and the biological sample measuring instrument,
      a control unit connected to the measurement unit, and
      a temperature information reception unit connected to the control unit, and the first temperature information supply instrument has:
      a temperature sensor, and
      a temperature information transmission unit which is connected to the temperature sensor and transmits the temperature information to the temperature information reception unit,
   the biological information measurement method comprising:
   the temperature information reception unit receiving the temperature information from the first temperature information supply instrument, after the biological sample measurement sensor is mounted to a sensor mounting portion provided in the biological sample measuring instrument; and
   the control unit correcting a measured value of the biological sample measured by the measurement unit according to the temperature information.
2. The biological information measurement method according to claim 1,
   wherein the temperature information reception unit receives the temperature information from the first temperature information supply instrument after a press temperature acquisition button arranged in the biological sample measuring instrument is pressed.
3. The biological information measurement method according to claim 1,
   wherein the temperature information reception unit performs communication by electric waves or light so as to receive the temperature information from the first temperature information supply instrument.

4. The biological information measurement method according to claim 1,
  wherein the temperature sensor is provided in an outer circumferential portion of the first temperature information supply instrument.

5. The biological information measurement method according to claim 1,
  wherein the first temperature information supply instrument and the biological sample measuring instrument are located at a distance that prevents interference with the temperature information between a second temperature information supply instrument and the biological sample measuring instrument when the temperature information reception unit receives the temperature information.

6. The biological information measurement method according to claim 1,
  wherein the biological sample measurement sensor is a separate component from the first temperature information supply instrument and the biological sample measuring instrument.

\* \* \* \* \*